US005725515A

United States Patent [19]
Propp

[11] Patent Number: 5,725,515
[45] Date of Patent: Mar. 10, 1998

[54] URINE SAMPLING AND BLADDER DRAINAGE SYSTEM

[75] Inventor: Donald J. Propp, Dewitt, Mich.

[73] Assignee: Tri-State Hospital Supply Corporation, Howell, Mich.

[21] Appl. No.: 604,262

[22] Filed: Feb. 21, 1996

Related U.S. Application Data

[63] Continuation of Ser. No. 332,882, Nov. 1, 1994, abandoned.

[51] Int. Cl.$^6$ .............................. A61M 1/00; A61F 5/44; A61B 5/00
[52] U.S. Cl. .................. 604/317; 601/323; 601/324; 601/327; 601/349; 128/760; 128/768
[58] Field of Search ................. 604/323, 327, 604/330, 328, 331, 326, 349; 128/760–764, 766–768

[56] References Cited

U.S. PATENT DOCUMENTS

| | | |
|---|---|---|
| 3,601,119 | 8/1971 | Engelsher . |
| 3,699,964 | 10/1972 | Ericson . |
| 3,906,935 | 9/1975 | Raia et al. ............................. 128/768 |
| 4,197,848 | 4/1980 | Garrett et al. . |
| 4,305,403 | 12/1981 | Dunn ...................................... 128/762 |
| 4,500,311 | 2/1985 | Redmond et al. . |
| 4,805,635 | 2/1989 | Korf et al. ............................. 128/767 |
| 4,902,282 | 2/1990 | Bellotti et al. . |
| 5,053,003 | 10/1991 | Dadson et al. . |
| 5,207,661 | 5/1993 | Repschlager . |
| 5,211,642 | 5/1993 | Clendenning . |
| 5,251,639 | 10/1993 | Rentsch ................................. 128/768 |
| 5,395,347 | 3/1995 | Blecher et al. ........................ 128/766 |

Primary Examiner—John G. Weiss
Assistant Examiner—Dennis Ruhl
Attorney, Agent, or Firm—Fildes & Outland, P.C.

[57] ABSTRACT

A urine sampling and bladder drainage system includes a tubing set having first, second, and third tube portions. Each tube portion has a first and second end, the first end of each tube portion being connected to and in communication with the first ends of the other two tube portions. A urinary catheter is connected to the second end of the first tube portion to permit inflow of urine into the tubing set during catheterization. A drainage device is connected to the second end of the second tube portion to permit collection of urine from the tubing set during draining. A removable sampling device independent of flow communication with the drainage device is connectable to the second end of the third tube portion to permit collection of urine from the tubing set during sampling. A first and second clamp at an intermediate location of the second and third tube portions respectively control urine flow through the tube portions to selectively communicate urine for draining or sampling.

7 Claims, 1 Drawing Sheet

URINE SAMPLING AND BLADDER DRAINAGE SYSTEM

This application is a continuation of application Ser. No. 08/332,882, filed Nov. 1, 1994 now abandoned.

FIELD OF THE INVENTION

This invention relates to urinary catheterization and more particularly to a system that provides a drainage device and a removable independent sampling device for selective urine collection for sampling most recently produced urine and bladder drainage during catheterization.

BACKGROUND OF THE INVENTION

It is known in the art relating to urinary catheterization to perform such catheterization to drain a patient's bladder and to obtain most recently produced urine samples for laboratory analysis.

Known urine drainage systems often include a urinary catheter connected to a collection/drainage device. The catheter may be maintained in a patient for days or weeks. Samplings are typically taken from the collection device for laboratory analysis. It has long been a problem that the urine samples from the collection device are not the most recently produced urine resulting in unreliable laboratory analysis and results. Therefore, it is common to exchange the collection device for a sampling device when a urine sample is desired.

This exchange involves interrupting the urine flow to the collection device, draining the collection device, removing the collection device from its communication with the catheter, connecting the sampling device in communication with the catheter, and establishing urine flow to the sampling device. After a urine sample is collected, in like fashion, the collection device must be exchanged for the sampling device. In addition to the exchange being a complicated procedure, the exchange of the collection device typically results in the spillage of urine and its contact with the patient or health care provider.

SUMMARY OF THE INVENTION

The present invention provides a urine sampling and bladder drainage system that allows selective urine collection for sampling to assure most recently produced uncontaminated urine for analysis, and urine drainage without the need to exchange the urine collection device with the sampling device. The present invention also provides a urine sampling device independent of and not in flow communication with the urine drainage device which is easily exchangeable to provide a sterile receptacle for a urine sample.

Accordingly, it is an object of this invention to simplify the procedures used for urine sampling and bladder drainage as well as eliminate the possibility of spilling urine during the shift in procedure from sampling to draining.

A more specific object of this invention is to provide a urine sampling and bladder drainage system including a tubing set having first, second, and third tube portions. Each tube portion has a first and second end. The first end of each tube portion is connected to and in communication with the first ends of the other two tube portions.

A urinary catheter connected to the second end of the first tube portion permits inflow of urine into the tubing set during catheterization. A drainage device connected to the second end of the second tube portion permits collection of urine from the tubing set during draining. A sampling device, independent of the drainage device and not in flow communication therewith, is removably connectable to the second end of the third tube portion and permits collection in a sterile receptacle of most recently produced urine from the tubing set during sampling. A first clamp at an intermediate location of the second tube portion is operable to control urine flow through the second tube portion and a second clamp at an intermediate location of the third tube portion is operable to control urine flow through the third tube portion. Through operation of the first and second clamps, urine is selectively communicable through the second and third tube portions for sampling or draining during catheterization as necessary, assuring most recently produced urine sampling without the necessity of exchanging collection and drainage devices.

These and other features and advantages of the invention will be more fully understood from the following detailed description of the invention taken together with the accompanying drawing.

DETAILED DESCRIPTION OF THE INVENTION

Figure 1:
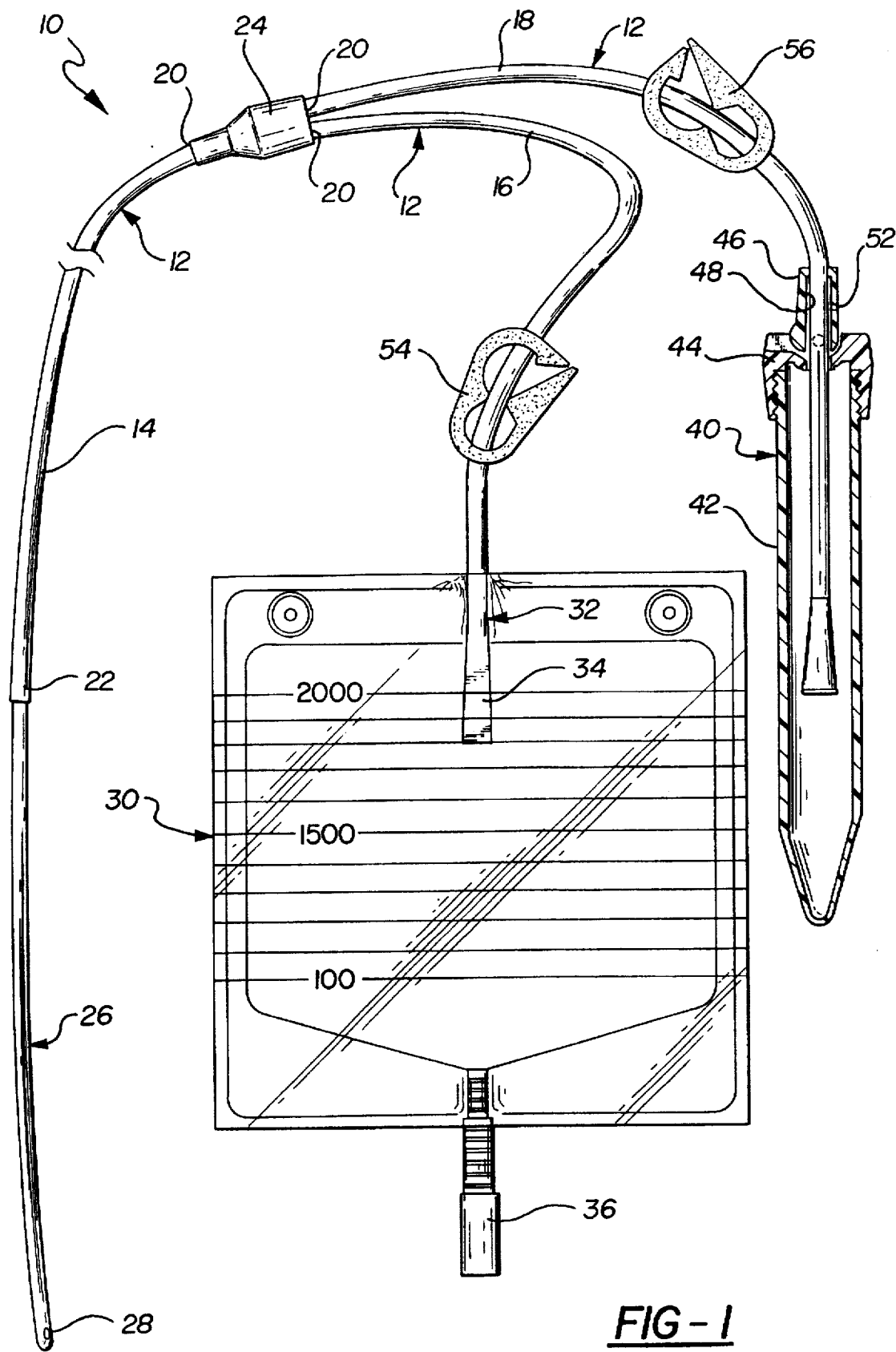
FIG. 1 is a perspective view of a urine sampling and bladder drainage system constructed in accordance with the present invention.

Referring now to the drawing in detail, numeral 10 generally indicates a urine sampling and bladder drainage system including a tubing set 12 having a first, second, and third plastic tube portions, 14, 16, 18, respectively. Each tube portion 14, 16, 18 has a first and second end 20, 22. The first end 20 of each tube portion 14, 16, 18 is connected to and in communication with the first ends of the other two tube portions. A bifurcation Y element 24 may be used to receive the first ends 20 of each of the tube portions 14, 16, 18.

A urinary catheter 26, suitable for sampling and/or drainage, is connected to the second end 22 of the first tube portion 14. Catheter 26 is provided with an inlet opening(s) 28 near the insertion end of the catheter to permit inflow of urine into the tubing set 12 during catheterization of a patient.

A drainage device 30, such as a disposable, flexible, thin-walled, plastic urinary drainage bag or other fluid receptacle, collects urine from the tubing set 12 during draining of the patient's bladder.

Drainage device 30 includes an inlet 32 connected to the second end 22 of the second tube portion 16 establishing a fluid connection with the tubing set 12. The inlet 32 may include a one-way valve 34 for preventing back flow of fluid and bacteria into the tubing set 12. One-way valve 34 is an anti-reflux flap valve or other one-way flow control valve. Drainage device 30 includes an outlet 36 to permit drainage of urine from the device. Outlet 36 has an open and closed position whereby in the open position the device 30 can be drained, and in the closed position urine is collectable in the device.

A sampling device 40 is removably connectable to the second end 22 of the third tube portion 18. Sampling device 40 includes a collection vessel 42 such as a lab sampling tube having an open end and a cap 44 in liquid sealing engagement with the tube open end. Cap 44 includes a spout 46 pivotally mounted on the cap for movement from an upright, opened position to a horizontal, closed position. Cap 44 is provided with an aperture which communicates with collection vessel 42 when the cap is secured on the collection vessel as is conventionally known.

Spout 46 is provided with an aperture 48 extending through the length of the spout so that when pivoted to the upright, opened position, the aperture is aligned and communicates with the aperture in the cap 44. When spout 46 is in the horizontal, closed position, the spout lies in a slot located in cap 44 and aperture 48 is no longer aligned with the aperture in the cap and there is no communication. Aperture 48 receives the end 22 of plastic tube portion 18 in frictional engagement, easily mounting the sampling device 40 to the tube portion 18.

Spout 46 is also provided with a vent aperture 52 extending through the side of the spout so that when the spout is in the upright, opened position, the vent aperture is in communication with the aperture in the cap. Vent aperture 52 vents the sampling device 40 during fluid collection for sampling as is readily apparent. In like fashion, when the spout 46 is in the horizontal, closed position, the vent aperture 52 is no longer in communication with the aperture in the cap and sealed against leakage.

Both the second and third tube portions 16, 18 have flow occluding clamps 54, 56 mounted intermediate the ends 20, 22 of the tube portions. Clamps 54, 56 can be opened to allow the passage of urine through the tube portions 16, 18, or closed to prohibit fluid flow.

The present system 10 is typically provided as a preassembled sterile system for obtaining a single urine sample for urinalysis. In such a system, the catheter 26 is inserted into the patient to begin the catheterization. Fluid received by the catheter is communicated through the tubing set 14. Clamp 54 is closed and clamp 56 is open to take the sample which is received in sampling device 40. When a sufficient sample has been received, clamp 56 is closed and clamp 54 is opened to allow the patient's bladder to finish draining into drainage device 30. During draining, the tube 18 can be pulled out of aperture 48, spout 46 closed, and the sample collected in sampling device 40 can be relocated for urinalysis along with the sampling device. At an appropriate time, the catheter 26 is withdrawn from the patient.

When system 10 is used as a long term drainage device, the catheter 26 is inserted into the patient to begin catheterization and through the opening and closing of clamps 54, 56, fluid is selectively allowed to pass to either drainage device 30 or sampling device 40.

Normally during draining, clamp 54 is in an open position allowing fluid to be communicated from the catheter 26 to the drainage device 30, and clamp 56 is in a closed position prohibiting the flow of urine to the second end 22 of third tube portion 18. When a urine sample for urinalysis is desired, a sterile sampling device 40 is easily fitted to the second end 22 of the third tube portion 18, by insertion of the third tube portion through aperture 48 in the opened position spout 46. Alternatively, cap 44 may be left in place and a fresh collection vessel 42 substituted for the filled collection vessel. In this case an extra non-spouted sealing cap can be used to seal the filled collection vessel 42.

Flow of only the most recently produced urine is directed into sampling device 40 by closing clamp 54 and opening clamp 56. When enough of a sample has been collected, clamp 56 is closed, the collection device 40 is removed from the second end 22 of the third tube portion 18, and the spout 46 is closed to seal the collected urine in the sampling device 40 for conveyance. Clamp 54 is opened and fluid is again collected in drainage device 30. Alternatively, a fresh collection vessel 42 is connected to cap 44 after removal of a used collection vessel from the cap. An extra non-spouted sealing cap is put on the used collection vessel 42 for transit to a lab. When another sample is needed, the procedure is repeated with another sterile sampling device 40 or vessel 42. The most recently produced urine is easily sampled without the complications and possibility of urine contamination of heretofore systems.

Although the invention has been described by reference to a specific embodiment, it should be understood that numerous changes may be made within the spirit and scope of the inventive concepts described. Accordingly, it is intended that the invention not be limited to the described embodiment, but that it have the full scope defined by the language of the following claims.

What is claimed is:

1. A urine sampling and bladder drainage system comprising:

a tubing set having first, second, and third tube portions, each tube portion having a first and second end, the first end of each tube portion being connected in bifurcated fashion to and in communication with the first ends of the other two tube portions;

a urinary catheter connected to the second end of the first tube portion permitting inflow of urine into said tubing set during catheterization;

a drainage device connected to the second end of the second tube portion permitting collection of urine from said tubing set during draining;

a removable sampling device vented to permit gravity flow connectable to the second end of the third tube portion permitting collection of urine from said catheter during sampling independent of flow communication with said drainage device;

a first clamping means at an intermediate location of said second tube portion to control urine flow through said second tube portion; and a second clamping means at an intermediate location of said third tube portion to control urine flow through said tube portion;

wherein urine is selectively communicable through said second and third tube portions for draining or sampling most recently produced urine during catheterization.

2. The invention of claim 1 wherein said drainage device comprises:

a urinary drainage bag of a disposable, thin-walled, plastic construction;

said drainage device including an inlet connected to said second end of said second tube portion providing for flow communication with said tubing set;

said drainage device also including an outlet having an open and closed position whereby said outlet in the open position allows said device to be drained through said outlet and in the closed position allows urine to be collected in said device.

3. The invention of claim 2 wherein said drainage device inlet includes a one way flow control valve.

4. The invention of claim 3 wherein said valve is an anti-reflux flap valve.

5. The invention of claim 1 wherein said removable sampling device is a collection receptacle comprising:

a lab sampling tube having an open end;

a cap fluid sealingly mountable on said tube open end;

said cap including a spout having an aperture therein for frictionally receiving the second end of the third tube portion for mounting said sampling device thereon and providing for flow communication with said tubing set;

said spout having an open and closed position whereby said spout in the open position provides access into the sampling tube to receive urine therein and in the closed position allows urine collected in said tube to be sealed therein after said third tube second end is removed from said spout.

6. The invention of claim 5 wherein said spout also includes a vent aperture therein providing a vent for the passage of air out of said tube as urine is received therein.

7. The invention of claim 1 where said first and second clamping means is a flow occluding clamp.

* * * * *